United States Patent [10] Patent No.: US 11,529,579 B2
Kawaguchi et al. (45) Date of Patent: Dec. 20, 2022

(54) FILTRATION DEVICE

(71) Applicant: Murata Manufacturing Co., Ltd., Nagaokakyo (JP)

(72) Inventors: Toshikazu Kawaguchi, Nagaokakyo (JP); Masaru Banju, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 360 days.

(21) Appl. No.: 16/751,649

(22) Filed: Jan. 24, 2020

(65) Prior Publication Data
US 2020/0155990 A1 May 21, 2020

Related U.S. Application Data

(63) Continuation of application No. PCT/JP2018/031304, filed on Aug. 24, 2018.

(30) Foreign Application Priority Data

Sep. 25, 2017 (JP) .............................. JP2017-183884

(51) Int. Cl.
*B01D 46/00* (2022.01)
*B01D 12/00* (2006.01)

(52) U.S. Cl.
CPC .......... *B01D 46/005* (2013.01); *B01D 12/00* (2013.01); *B01D 2201/32* (2013.01); *B01D 2311/04* (2013.01); *B01D 2311/25* (2013.01)

(58) Field of Classification Search
CPC . B01D 46/005; B01D 2201/32; A61M 1/3635
See application file for complete search history.

(56) References Cited

U.S. PATENT DOCUMENTS 4,009,715 A 3/1977 Forberg et al.
4,274,285 A 6/1981 Purgold
(Continued)

FOREIGN PATENT DOCUMENTS

CN 201669063 U 12/2010
JP H0657254 B2 8/1994
(Continued)

OTHER PUBLICATIONS

International Search Report issued for PCT/JP2018/031304, dated Nov. 27, 2018.
(Continued)

*Primary Examiner* — Bradley R Spies
(74) *Attorney, Agent, or Firm* — ArentFox Schiff LLP

(57) ABSTRACT

A filtration device includes a first channel member, a second channel member, and a filter. The first channel member has a recess recessed inward from an outer wall surface. A groove is formed is the recess and has an opening in a recessed surface of the recess. First and second channels, each defined by a through-hole, are formed in the first channel member and are connected to the groove. A first connection part connects the groove with the first channel. The second channel member has a projection that detachably mates with the recess. The second channel member includes a discharge channel that has an opening in a projecting surface of the projection, the opening being located over the groove. The filter is disposed along the groove, and positioned at the opening of the discharge channel. When the first and second channel members are placed in a operative relationship, a third channel is formed by the projecting surface of the projection and the opening of the groove. The third channel is connected to the first channel via the first connection part. The third channel at which the filter is
(Continued)

positioned has a smaller cross-sectional area than the first channel.

12 Claims, 10 Drawing Sheets

(56) References Cited

U.S. PATENT DOCUMENTS

| | | | |
|---|---|---|---|
| 5,914,042 A | 6/1999 | Ball et al. |
| 6,159,232 A | 12/2000 | Nowakowski |
| 6,274,090 B1 | 8/2001 | Coelho et al. |
| 7,056,722 B1 | 6/2006 | Coelho et al. |
| 7,650,805 B2 | 1/2010 | Nauseda et al. |
| 9,925,333 B2 | 3/2018 | Hooven et al. |
| 10,584,078 B2 | 3/2020 | Franci |
| 2006/0079834 A1 | 4/2006 | Tennican et al. |
| 2007/0079649 A1 | 4/2007 | Nauseda et al. |
| 2013/0225903 A1 | 8/2013 | Franci et al. |
| 2013/0264295 A1 | 10/2013 | Lee |
| 2015/0083665 A1 | 3/2015 | Oranth |
| 2016/0144105 A1 | 5/2016 | Hooven et al. |
| 2016/0257622 A1 | 9/2016 | Franci |
| 2018/0161497 A1 | 6/2018 | Hooven et al. |

FOREIGN PATENT DOCUMENTS

| | | |
|---|---|---|
| JP | 2003517272 A | 5/2003 |
| JP | 2006115775 A | 5/2006 |
| JP | 2007105725 A | 4/2007 |
| JP | 2008515594 A | 5/2008 |
| JP | 2009106881 A | 5/2009 |
| JP | 2013217918 A | 10/2013 |
| JP | 2015516289 A | 6/2015 |
| JP | 2016524513 A | 8/2016 |
| JP | 6137438 B1 | 5/2017 |
| WO | 8909646 A1 | 10/1989 |
| WO | 2006130815 A2 | 12/2006 |
| WO | 2013098487 A1 | 7/2013 |
| WO | 2015071288 A1 | 5/2015 |
| WO | 2017104261 A1 | 6/2017 |

OTHER PUBLICATIONS

Written Opinion of the International Searching Authority issued for PCT/JP2018/031304, dated Nov. 27, 2018.
International Search Report issued for PCT/JP2018/032626, dated Nov. 27, 2018.
Written Opinion of the International Searching Authority issued for PCT/JP2018/032626, dated Nov. 27, 2018.

FILTRATION DEVICE

CROSS REFERENCE TO RELATED APPLICATIONS

The present application is a continuation of International application No. PCT/JP2018/031304, filed Aug. 24, 2018, which claims priority to Japanese Patent Application No. 2017-183884, filed Sep. 25, 2017, the entire contents of each of which are incorporated herein by reference.

TECHNICAL FIELD

The present invention relates to a filtration device that separates a target substance included in a fluid from the fluid.

BACKGROUND OF THE INVENTION

Japanese Examined Patent Application Publication No. 6-57254 (hereinafter "Patent Document 1") discloses a filtration device with a circulating system. The circulating system includes a container containing a liquid including blood components, and a ceramic filter. The filtration device is used for cross-flow filtration of the liquid including blood components.

The filtration device disclosed in Patent Document 1 has problems described below. If the fluid to be filtered has low velocity, the target substance does not readily detach from the filter after coming into contact with the filter, and is thus likely to clog the filter. By contrast, if the fluid has high velocity across the entire flow channel, the fluid tends to bubble.

The present invention aims to address the above-mentioned problems by providing a filtration device that reduces clogging of a filter by a target substance, and reduces bubbling of a fluid.

BRIEF SUMMARY OF THE INVENTION

A filtration device comprising:
(a) a first channel member including:
(i) a recess recessed inward from an outer wall surface;
(ii) a groove formed in a recessed surface of the recess, the groove having an opening;
(iii) first and second channels defined by respective through-holes connected to the groove;
(iv) a first connection part connecting the groove with the first channel; and
(v) a second connection part connecting the groove with the second channel;
(b) a second channel member removably connected to the first channel member, the second channel member having a projection which includes a projection surface that cooperates with the recess of the first channel member to define a third channel located between the first and second channels of the first channel member, the third channel being connected to the first channel via the first connection part, and being connected to the second channel via the second connection part, the third channel having a smaller cross-sectional area than the first channel, the second channel member including a discharge channel located in the projection and having an opening that extends through the projection surface; and
(c) a filter positioned at the opening of the discharge channel such that the filter is located along the third channel.

The above-mentioned configuration makes it possible to minimize an increase in the velocity of the fluid across the entire channel while increasing the velocity of the fluid through the third channel that faces the filter. This helps reduce clogging of the filter by the target substance, and also reduce bubbling of the fluid (liquid) to be filtered. If the target substance is a cell, the above-mentioned configuration also helps minimize a decrease in the activity of the cell or damage to the cell.

In one possible configuration of the filtration device, the recess and the projection are detachably mated with each other without using another intervening component.

The above-mentioned configuration eliminates the need for a screw or other such component. The second channel member can be thus easily attached to or detached from the first channel member.

In one possible configuration of the filtration device,
the first channel member has a recessed mating surface on a lateral side of the recess to allow mating between the recess and the projection,
the second channel member has a projecting mating surface on a lateral side of the projection to allow mating between the recess and the projection,
the recessed mating surface includes a notch recessed inwardly of the first channel member,
the projecting mating surface includes a protrusion, the protrusion protruding outwardly of the second channel member to mate with the notch, and
the second channel member is detachably attached to the first channel member by mating the protrusion with the notch.

The above-mentioned configuration facilitates detachably attaching the second channel member to the first channel member.

In one possible configuration of the filtration device,
the recessed mating surface defines a sloped surface inclined with respect to the recessed surface of the recess,
the projecting mating surface defines a sloped surface inclined with respect to the projecting surface of the projection that contacts the recessed surface of the recess, and
the first channel member and the second channel member are mated with each other by bringing the recessed mating surface and the projecting mating surface into surface contact with each other.

The above-mentioned configuration helps ensure that, at the location of the lateral side of the recess, the first channel member and the second channel member make contact over an increased area. This helps further reduce leakage of the fluid flowing in the first channel member.

In one possible configuration of the filtration device,
the recessed surface of the recess of the first channel member defines a flat surface,
the projecting surface of the projection of the second channel member defines a flat surface, and
the first channel member and the second channel member are mated with each other by bringing the recessed surface of the recess and the projecting surface of the projection into surface contact with each other.

The above-mentioned configuration helps ensure that, at the location of the recessed surface of the recess, the first channel member and the second channel member make contact over an increased area. This helps further reduce leakage of the fluid flowing in the first channel member.

In one possible configuration of the filtration device,
the filter has a first major surface and a second major surface that face each other,
the first major surface is disposed adjacent to the third channel, the second major surface is disposed adjacent to the discharge channel, and the first major surface and the projecting surface are flush with each other.

The above-mentioned configuration helps increase the velocity at which the fluid flows near the filter.

In one possible configuration of the filtration device, the second channel has a larger cross-sectional area than the third channel.

The above-mentioned configuration helps minimize an increase in flow velocity through the second channel.

In one possible configuration of the filtration device, the filter is attached to the second channel member.

The above-mentioned configuration allows the filter to be easily replaced by detaching the second channel member from the first channel member.

In one possible configuration of the filtration device, the groove is provided linearly.

The above-mentioned configuration helps increase the velocity of fluid flow through the groove.

In one possible configuration of the filtration device, the first channel member includes a plurality of recesses, and each recess mates with the second channel member to which the filter is attached.

The above-mentioned configuration makes it possible to use a plurality of filters to filter the fluid.

In one possible configuration of the filtration device, the second channel member includes a plurality of discharge channels each having the opening, and the filter is positioned at the opening of each discharge channel.

The above-mentioned configuration makes it possible to use a plurality of filters to filter the fluid.

The present invention makes it possible to reduce clogging of a filter by a target substance, and reduce bubbling of a fluid.

DESCRIPTION OF THE PREFERRED EMBODIMENTS

Figure 1:
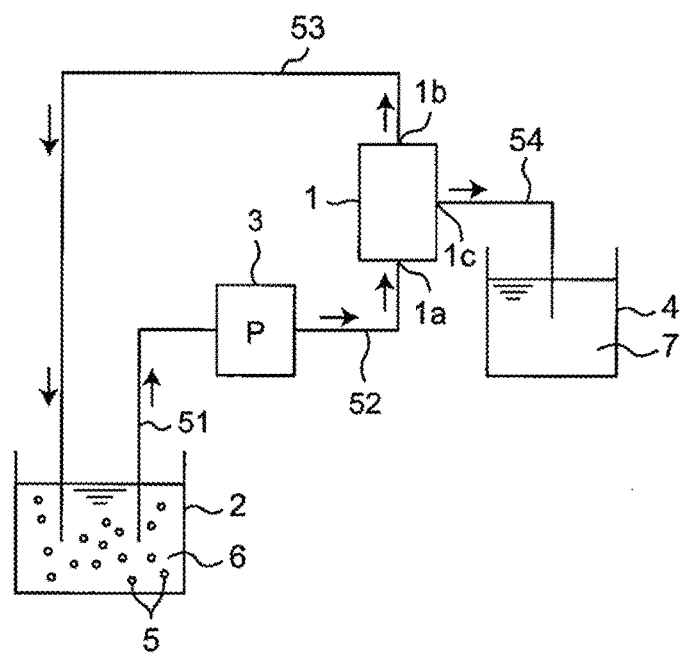
FIG. 1 schematically illustrates an example of how a target substance is separated by filtration using a filtration device according to an exemplary embodiment (Embodiment 1) of the present invention.

In cross-flow filtration devices, a filter is provided along the flow of the fluid to be filtered, and the fluid is filtered through the filter. If the fluid has low velocity, the target substance does not readily detach from the filter after coming into contact with the filter, and is thus likely to clog the filter. One way to reduce such clogging would be to increase the velocity of the fluid. However, increasing the velocity of the fluid across the entire flow channel can make the fluid more susceptible to bubbling if the fluid is, for example, a culture medium. If the target substance is a cell, the increased fluid velocity can cause a decrease in the activity of the cell or damage to the cell.

Accordingly, the present inventors have found that, by making the cross-sectional area smaller in a portion of the flow channel facing the filter than in other portions, the velocity of the fluid through the channel portion facing the filter is increased while minimizing an increase in the velocity of the fluid across the entire channel. The term "entire channel" is used herein to include, for example, a channel within the filtration device that has a larger cross-sectional area than in the channel portion facing the filter, a channel (piping) connected to the filtration device, and a pump connected to such a channel. The present inventors have found that the above-mentioned configuration can reduce clogging of the filter by the target substance, and also reduce bubbling of the fluid to be filtered if the fluid is a liquid. The present inventors have also found that if the target substance is a cell, the above-mentioned configuration can minimize a decrease in the activity of the cell or damage to the cell.

An embodiment of the present invention will be described below with reference to the accompanying drawings. In the drawings, the elements are shown in exaggerated form for ease of description.

Embodiment 1

FIG. 1 schematically illustrates an example of how a target substance 5 is separated by filtration using a filtration device 1 according to Embodiment 1 of the present invention. As illustrated in FIG. 1, the filtration device 1 is a cross-flow filtration device. The filtration device 1 admits a fluid 6 including the target substance 5 through a fluid inlet 1a, and discharges the fluid 6 through a fluid outlet 1b. The filtration device 1 filters a portion of the fluid 6 flowing from the fluid inlet 1a to the fluid outlet 1b, and discharges, through a filtrate outlet 1c, a fluid (to be referred to hereafter as filtrate) 7 from which the target substance 5 has been removed by the filtration.

The fluid 6 including the target substance 5 is received in a fluid tank 2. The fluid 6 in the fluid tank 2 is drawn into a pump 3 through a pipe 51, and then supplied by the pump 3 to the fluid inlet 1a of the filtration device 1 through a pipe 52. The fluid 6 discharged through the fluid outlet 1b after passing through the filtration device 1 is returned into the fluid tank 2 through a pipe 53. In this way, while the pump 3 is in operation, the fluid 6 circulates through the fluid tank 2, the pipe 51, the pump 3, the pipe 52, the filtration device 1, and the pipe 53 in this order.

A portion of the fluid 6 supplied into the filtration device 1 is filtered, and discharged as the filtrate 7 through the filtrate outlet 1c. The filtrate 7 discharged through the filtrate outlet 1c is placed into a filtrate tank 4 through a pipe 54.

The term "target substance" as used herein refers to, among substances included in a fluid, a substance to be separated by filtration. For example, the target substance may be a biologically derived substance included in a fluid. The term "biologically derived substance" as used herein refers to a substance derived from living organisms such as cells (eukaryotes), bacteria (eubacteria), or viruses. Examples of cells (eukaryotes) include induced pluripotent stem cells (iPS cells), ES cells, stem cells, mesenchymal stem cells, mononuclear cells, single cells, cell clusters, suspension cells, adherent cells, nerve cells, white blood cells, cells for regenerative medicine, autologous cells, cancer cells, circulating tumor cells in blood (CTC), HL-60, HELA, and fungi. Examples of bacteria (eubacteria) include *E. coli*, and *Mycobacterium tuberculosis*. The term "fluid" means a liquid. In Embodiment 1, the fluid is preferably a cell culture solution, and the target substance is preferably a cell (eukaryote). Since cells are prone to deformation during filtration, the filtration device 1 according to the present invention is particularly suitable for filtration involving a cell as a target substance.

The configuration of the filtration device 1 will be described below in more detail.

[General Arrangement]

Figure 2A:
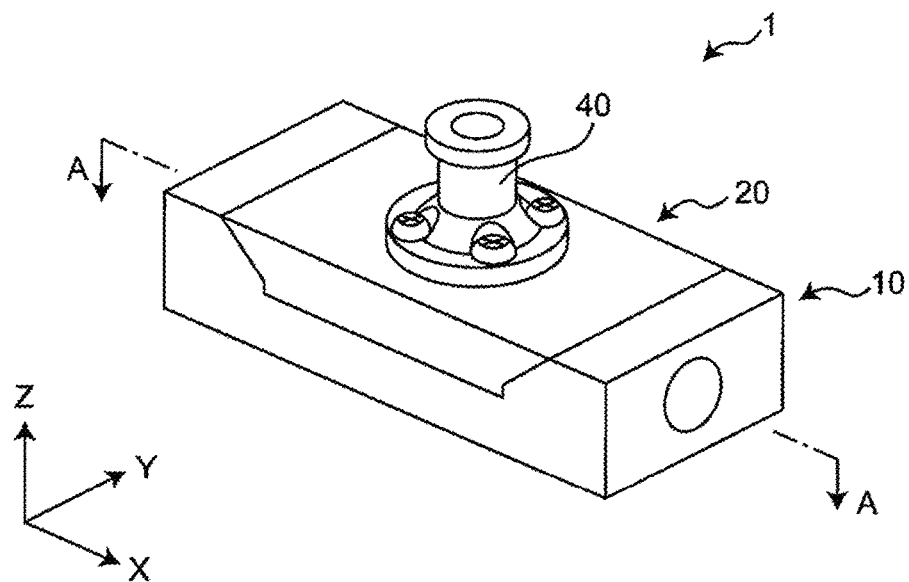
FIG. 2A is a schematic perspective view of the filtration device according to Embodiment 1 of the present invention.
Figure 2B:
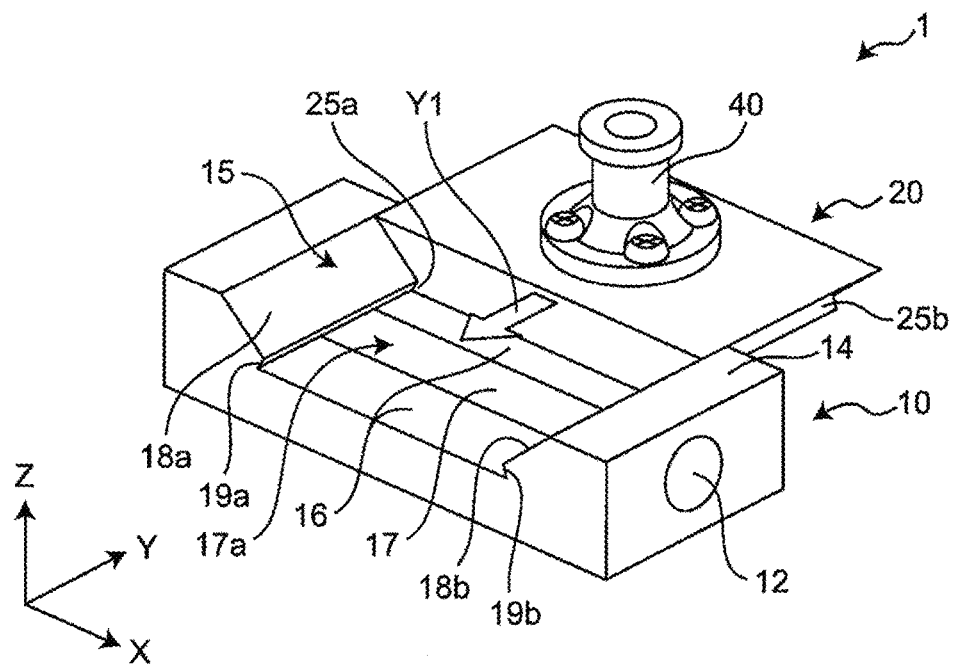
FIG. 2B is a perspective view of the filtration device according to Embodiment 1 of the present invention, illustrating an example of how a second channel member is attached to a first channel member.
Figure 3:
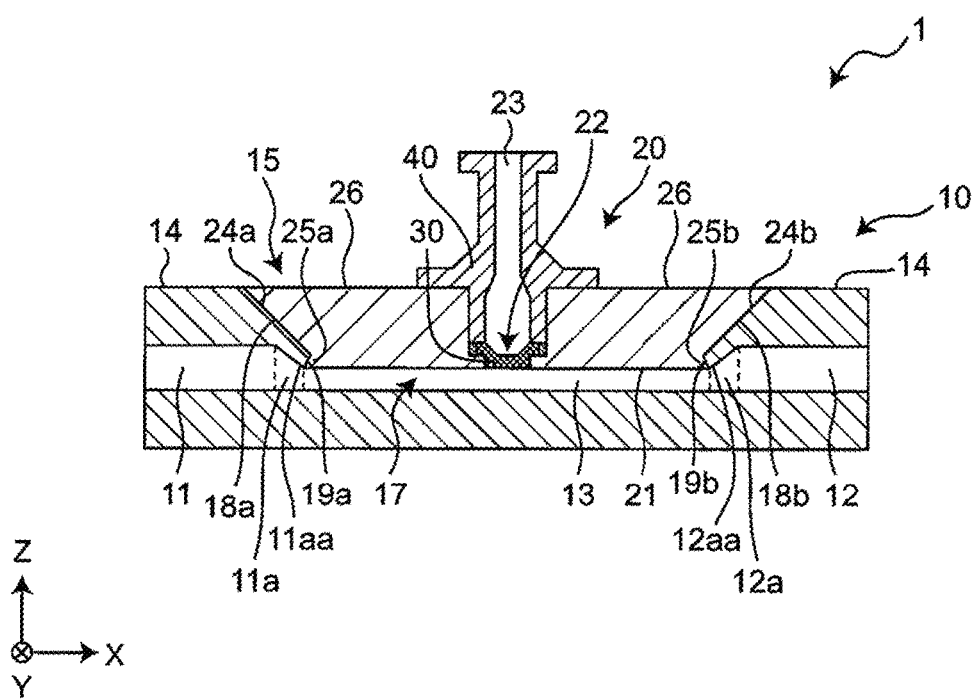
FIG. 3 is a cross-sectional view taken along a line A-A in FIG. 2A.

FIG. 2A is a schematic perspective view of the filtration device 1 according to Embodiment 1 of the present invention. FIG. 2B is a schematic perspective view of the filtration device 1, illustrating how a second channel member 20 is attached to a first channel member 10. FIG. 3 is a cross-section taken along a line A-A in FIG. 2A. As illustrated in FIGS. 2A and 3, the filtration device 1 includes the first channel member 10, the second channel member 20 that detachably mates with the first channel member 10, and a filter 30 attached to the second channel member 20. In Embodiment 1, the filter 30 is attached to the second channel member 20 by fastening a holder 40 with a screw or other such fastening component. Hereinafter, the X, Y, and Z directions in the drawings respectively represent the lateral, longitudinal, and height directions of the filtration device 1.

As illustrated in FIG. 2B, in Embodiment 1, the second channel member 20 is attached to the first channel member 10 by sliding the second channel member 20 in a Y1 direction relative to the first channel member 10.

As illustrated in FIG. 3, the filtration device 1 includes a first channel 11, a second channel 12, and a third channel 13. The first channel 11 and the second channel 12 are each defined by a through-hole. The first channel 11 and the third channel 13 are connected via a first connection part 11a. The second channel 12 and the third channel 13 are connected via a second connection part 12a. The third channel 13, which corresponds to the filtration portion in Embodiment 1, has a smaller cross-sectional area than the first and second channels 11 and 12. In Embodiment 1, the first channel 11 and the second channel 12 preferably have the same cross-sectional area. The term cross-sectional area as used herein refers to the cross-sectional area of a channel taken along a direction orthogonal to the direction in which the channel extends.

<First Channel Member>

Figure 4A:
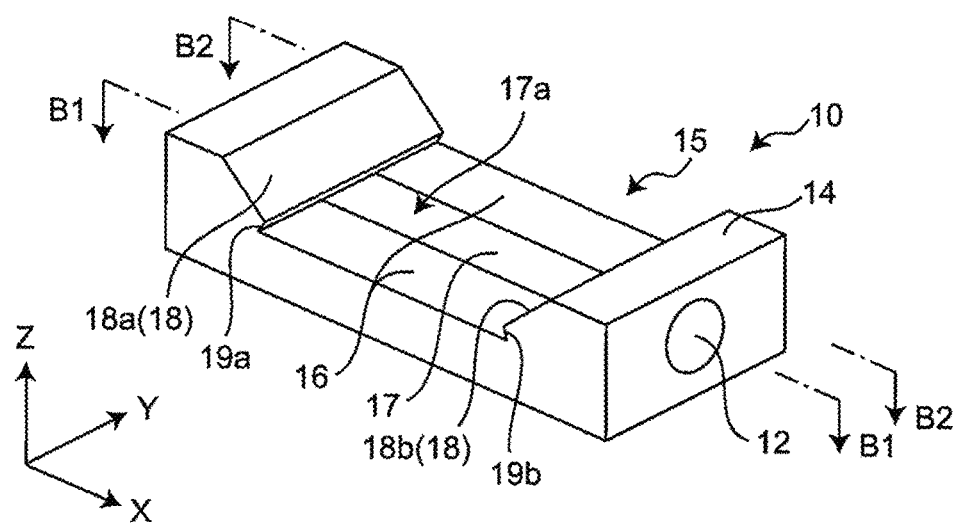
FIG. 4A is a schematic perspective view of the first channel member of the filtration device according to Embodiment 1 of the present invention.
Figure 4B:
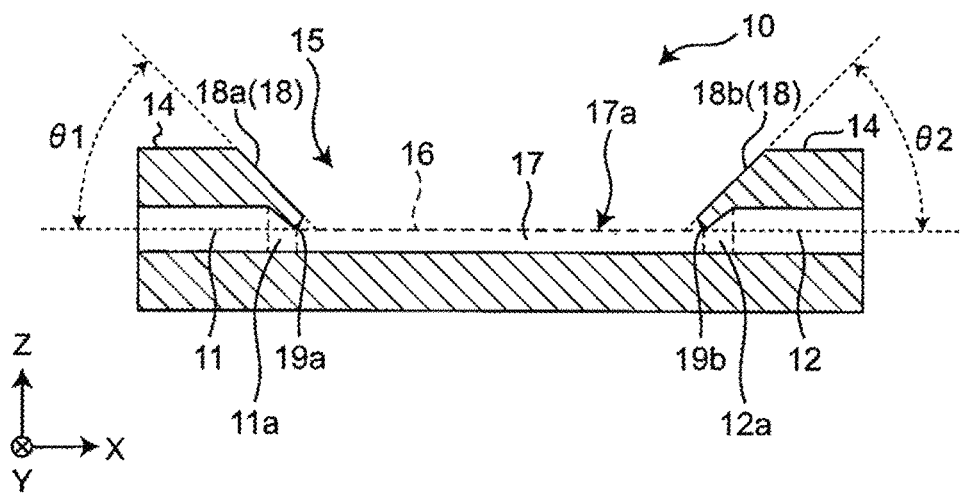
FIG. 4B is a cross-sectional view taken along a line B1-B1 in FIG. 4A.
Figure 4C:
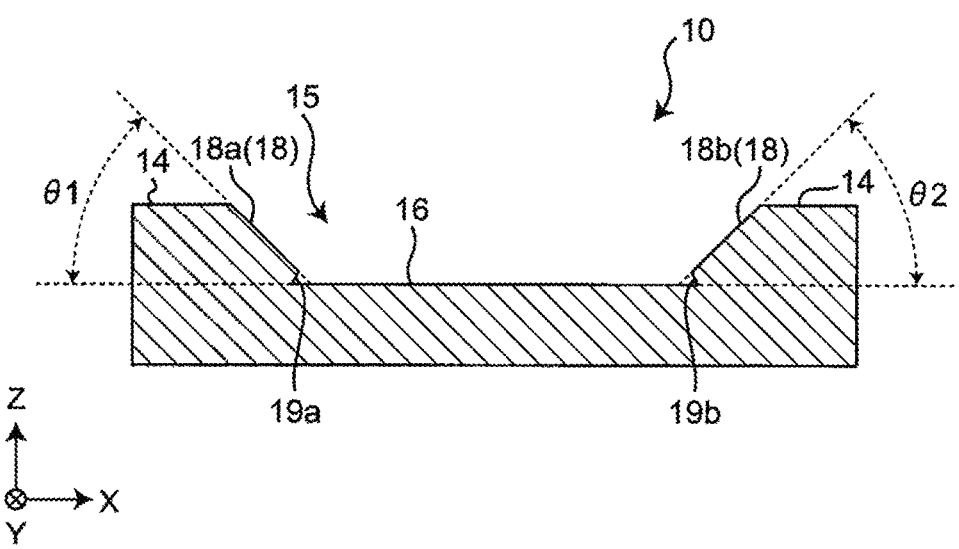
FIG. 4C is a cross-sectional view taken along a line B2-B2 in FIG. 4A.

FIG. 4A is a schematic perspective view of the first channel member 10 of the filtration device 1 according to Embodiment 1 of the present invention. FIG. 4B is a cross-section taken along a line B1-B1 in FIG. 4A. FIG. 4C is a cross-section taken along a line B2-B2 in FIG. 4A.

As illustrated in FIGS. 4A to 4C, the first channel member 10 has a recess 15, a groove 17, and the first and second channels 11 and 12. The recess 15 is recessed inward from an first outer wall surface 14. The groove 17 has an opening 17a in a recessed surface 16 of the recess 15. The first and second channels 11 and 12 are each defined by a through-hole connected to the groove 17. The first channel member 10 also has the first connection part 11a that connects the groove 17 with the first channel 11, and the second connection part 12a that connects the groove 17 with the second channel 12. More specifically, the first channel member 10 has the recess 15 that is recessed inward (−Z direction) from the first outer wall surface 14, which is a flat surface, and also includes the first and second channels 11 and 12 defined therein. With the first outer wall surface 14 of the first channel member 10 defined as first outer wall surface 14, a second outer wall surface opposite to the first outer wall surface 14 is formed parallel to the first outer wall surface 14. The first channel 11 extends in the −X direction, and the second channel 12 extends in the +X direction. This configuration helps reduce the height (length in the Z direction) of the first channel member 10. The first and second channels 11 and 12 are formed in the shape of a circular tube.

The recessed surface 16 of the recess 15 of the first channel member 10 defines a flat surface. The recessed surface 16 of the recess 15 is provided with the groove 17 connected to the first and second channels 11 and 12. The groove 17 has a recessed configuration. The groove 17 has the opening 17a in the recessed surface 16 of the recess 15. The groove 17 is formed linearly. In Embodiment 1, the groove 17 has a semi-circular cross-section when taken in the Y direction. The groove 17 extends linearly in the X direction.

The first and second channels 11 and 12 are connected to the groove 17. The first channel 11 is connected to the groove 17 via the first connection part 11a. The second channel 12 is connected to the groove 17 via the second connection part 12a. In the first connection part 11a between the first channel 11 and the groove 17, and in the second connection part 12a between the second channel 12 and the groove 17, the first and second channels 11 and 12 decrease in cross-sectional area with increasing proximity to the groove 17. More specifically, the first connection part 11a defines a first sloped surfaced surface 11aa that connects the first channel 11 with one end of the groove 17. The second connection part 12a defines a second sloped surfaced surface 12aa that connects the second channel 12 with the other end of the groove 17. The first sloped surfaced surface 11aa is inclined so as to narrow the first channel 11. The second sloped surfaced surface 12aa is inclined so as to enlarge the groove 17.

The first channel member 10 has a recessed mating surface 18 on the lateral side of the recess 15 to allow mating between the recess 15 and a projection 27 described later. The recessed mating surface 18 defines a sloped surface inclined with respect to the recessed surface 16 of the recess 15. In Embodiment 1, the recessed mating surface 18 includes a first sloped surface 18a, and a second sloped surface 18b. The angle θ1 formed by the first sloped surface 18a and the recessed surface 16, and the angle θ2 formed by the second sloped surface 18b and the recessed surface 16 are, for example, 45 degrees.

As illustrated in FIGS. 4B and 4C, the recessed mating surface 18 includes notches 19a and 19b recessed inwardly of the first channel member 10. More specifically, the first sloped surface 18a includes, in its end portion adjacent to the recessed surface 16, a first notch 19a notched in a direction in which the first channel 11 extends (−X direction). The second sloped surface 18b includes, in its end portion adjacent to the recessed surface 16, a second notch 19b notched in a direction (+X direction) in which the second channel 12 extends. The first notch 19a is inclined with respect to the Z-axis by, for example, two degrees in the +X direction, and the second notch 19b is inclined with respect to the Z-axis by, for example, two degrees in the −X direction.

The lateral side of the recess 15 transverse to the third channel 13 is open. In Embodiment 1, the lateral side of the recess 15 in a direction (Y direction) orthogonal to the third channel 13 is open. Thus, as illustrated in FIG. 2B, in mating the first and second channel members 10 and 20 with each other, the second channel member 20 can be inserted into the first channel member 10 from the open lateral side of the recess 15 by sliding the second channel member 20 in a direction (Y1 direction) transverse (e.g., orthogonal) to the direction (X direction) in which the groove 17 extends. At this time, as illustrated in FIG. 3, the second channel member 20 slides relative to the first channel member 10 in a state in which first and second protrusions 25a and 25b of the second channel member 20, which will be described later, are respectively mated with the first and second notches 19a and 19b. By sliding the second channel member 20 relative to the first channel member 10, the second channel member 20 can be easily attached to or detached from the first channel member 10. It is to be noted that the first notch 19a and the second notch 19b are depicted in exaggerated form in the drawings.

The first channel member 10 is made of, for example, polymethyl methacrylate (PMMA), or polystyrene (PS), or polyphenylene sulfide (PPS).

<Second Channel Member>

Figure 5A:
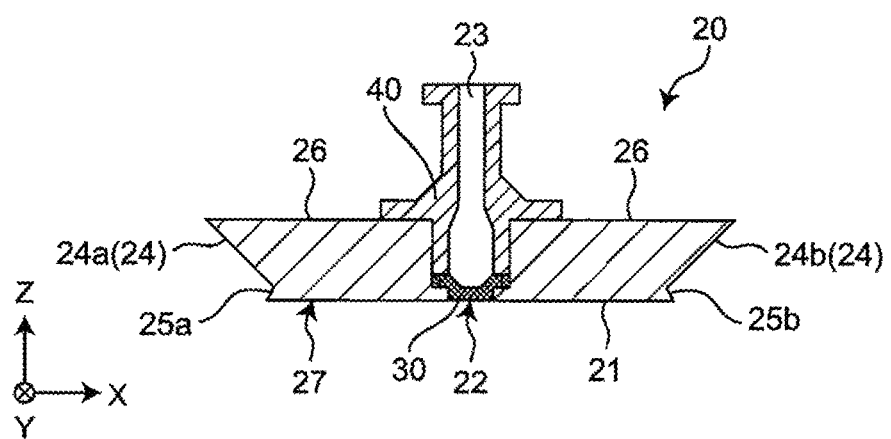
FIG. 5A is a schematic cross-sectional view of the second channel member of the filtration device according to Embodiment 1 of the present invention.
Figure 5B:
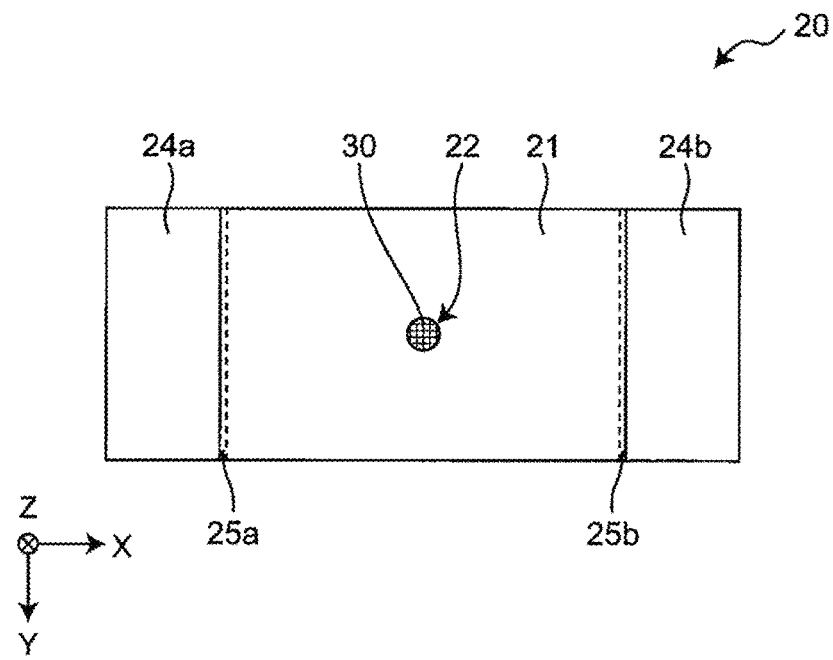
FIG. 5B is a schematic view, as seen from a projecting surface, of the second channel member of the filtration device according to Embodiment 1 of the present invention.

FIG. 5A is a schematic cross-sectional view of the second channel member 20 of the filtration device 1 according to Embodiment 1 of the present invention. FIG. 5B is a schematic view, as seen from a projecting surface 21, of the second channel member 20 of the filtration device 1 according to Embodiment 1 of the present invention. FIGS. 5A and 5B each schematically illustrate the configuration of the second channel member 20 with the filter 30 attached to the second channel member 20.

The second channel member 20 has the projection 27 that detachably mates with the recess 15 of the first channel member 10. The recess 15 and the projection 27 are detachably mated with each other without using another intervening component such as a screw. As illustrated in FIGS. 5A and 5B, the projecting surface 21 of the projection 27 of the second channel member 20 that contacts the recessed surface 16 of the recess 15 defines a flat surface. The second channel member 20 includes a discharge channel 23 extending in the Z direction. The discharge channel 23 has an opening 22 in the projecting surface 21 of the projection 27 placed over the groove 17. The filter 30 is positioned at the opening 22.

The second channel member 20 has a projecting mating surface 24 on the lateral side of the projection 27 to allow mating between the recess 15 and the projection 27. The projecting mating surface 24 defines a sloped surface inclined with respect to the projecting surface 21 of the projection 27 that contacts the recessed surface 16 of the recess 15. In Embodiment 1, the projecting mating surface 24 has a third sloped surface 24a, and a fourth sloped surface 24b. The third sloped surface 24a engages in mating relation with the first sloped surface 18a, and the fourth sloped surface 24b engages in mating relation with the second sloped surface 18b.

The projecting mating surface 24 includes protrusions 25a and 25b, which protrude outwardly of the second channel member 20 and respectively mate with the notches 19a and 19b. More specifically, the third sloped surface 24a includes a first protrusion 25a that mates with the first notch 19a of the first channel member 10, and the fourth sloped surface 24b includes a second protrusion 25b that mates with the second notch 19b. The first protrusion 25a protrudes in the −X direction, and the second protrusion 25b protrudes in the +X direction. The sloped surface of the first protrusion 25a is inclined with respect to the Z-axis by, for example, two degrees in the +X direction, and the sloped surface of the second protrusion 25b is inclined with respect to the Z-axis by, for example, two degrees in the −X direction. It is to be noted that the first protrusion 25a and the second protrusion 25b are depicted in exaggerated form in the drawings.

The following describes, with reference to FIG. 3, the mating between the recess 15 of the first channel member 10 and the projection of the second channel member 20. The second channel member 20 is detachably attached to the first channel member 10 by mating the first protrusion 25a with the first notch 19a and mating the second protrusion 25b with the second notch 19b. This configuration helps keep the second channel member 20 from disengaging from the first channel member 10 in the Z direction. At this time, the mating between the first channel member 10 and the second channel member 20 is achieved by bringing the recessed surface 16 of the recess 15 (see FIG. 4A) and the projecting surface 21 of the projection 27 (see FIG. 5A) into surface contact with each other. Further, the mating between the first channel member 10 and the second channel member 20 is achieved by bringing the first sloped surface 18a and the third sloped surface 24a into surface contact with each other, and bringing the second sloped surface 18b and the fourth sloped surface 24b into surface contact with each other. The first outer wall surface 14 of the first channel member 10 is flush (planar) with an outer wall surface 26 of the second channel member 20 located opposite to the projecting surface 21 of the projection 27.

As illustrated in FIG. 3, the third channel 13 is formed by positioning the projecting surface 21 of the projection 27 of the second channel member 20 over the opening 17a of the groove 17 of the first channel member 10. In other words, the groove 17 forms the third channel 13, which is semicircular in cross section, when the second channel member 20 is mated with the recess 15 of the first channel member 10. The third channel 13 faces the filter 30 positioned at the opening 22 of the discharge channel 23 in the second channel member 20, and extends in the X direction.

The third channel 13 is connected to the first channel 11 via the first connection part 11a, and connected to the second channel 12 via the second connection part 12a. More specifically, the third channel 13 is connected to the first channel 11 via the first sloped surfaced surface 11aa of the first connection part 11a, and connected to the second channel 12 via the second sloped surfaced surface 12aa of the second connection part 12a. The first sloped surfaced surface 11aa and the second sloped surfaced surface 12aa are respectively inclined such that the first channel 11 and the second channel 12 decrease in cross-sectional area with increasing proximity to the third channel 13. This configuration helps prevent an abrupt change in the velocity of fluid flow from the first channel 11 to the third channel 13, and an abrupt change in the velocity of fluid flow from the third channel 13 to the second channel 12.

Figure 6:
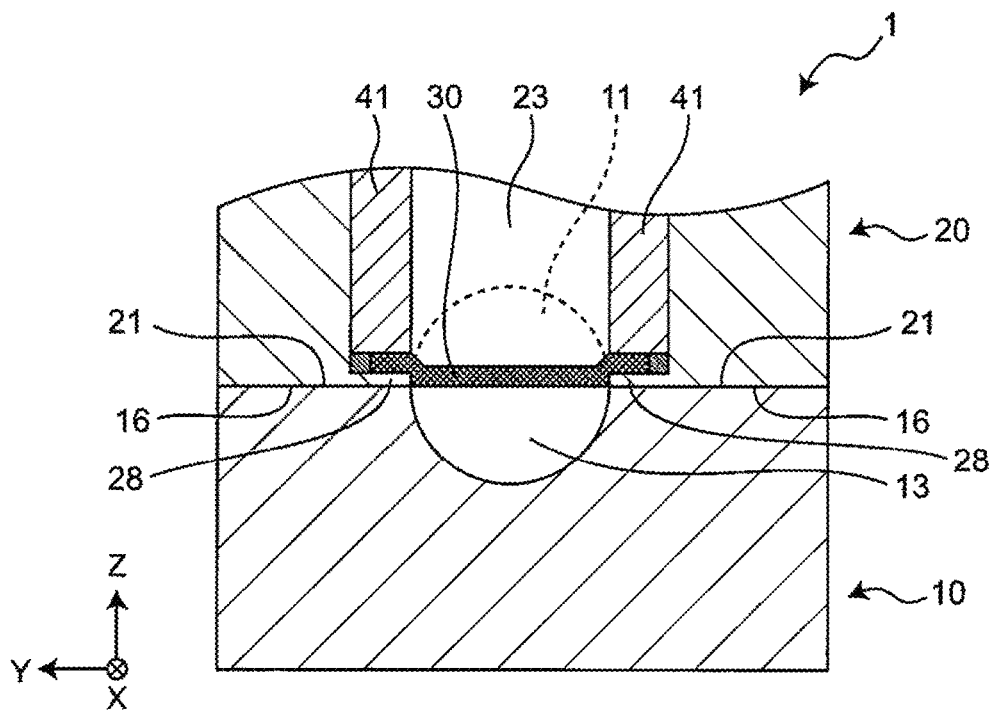
FIG. 6 is a longitudinal sectional view, taken in the Y direction at the location of a filter, of a portion of the filtration device according to Embodiment 1 of the present invention.

FIG. 6 is a longitudinal sectional view, taken in the Y direction at the location of the filter 30, of a portion of the filtration device 1 according to Embodiment 1 of the present invention. As illustrated in FIG. 6, the third channel 13 has a smaller cross-sectional area than the first and second channels 11 and 12. More specifically, the third channel 13 at which the filter 30 is positioned has a smaller cross-sectional area than the first channel 11. In other words, the portion of the third channel 13 where the filter 30 is positioned has a smaller cross-sectional area than the first channel 11. In the present exemplary embodiment, the third channel 13 has half the cross-sectional area of each of the first and second channels 11 and 12, which are in the shape of a circular tube. More specifically, the third channel 13 extends in the same direction (X direction) as the first channel 11, and is formed in the shape of a semi-circular tube with a semi-circular cross-section. The third channel 13 thus has the same cross-sectional shape as the lower half of each of the first and second channels 11 and 12. This configuration helps prevent an abrupt change in the velocity of fluid flow from the first channel 11 to the third channel 13, and an abrupt change in the velocity of fluid flow from the third channel 13 to the second channel 12. The above-mentioned configuration, in which the first and second channels 11 and 12 are formed in the shape of a circular tube and the third channel 13 is formed in the shape of a semi-circular tube, can also help reduce accumulation of the target substance at the bottom.

The second channel member 20 is made of, for example, polyoxymethylene (POM), polypropylene (PP), or polyether ether ketone (PEEK). There are, for example, four possible combinations of the first channel member 10 and the second channel member 20 described below. In a first combination, the first channel member 10 is made of polystyrene, and the second channel member 20 is made of polypropylene. In a second combination, the first channel member 10 is made of polymethyl methacrylate, and the second channel member 20 is made of polyoxymethylene. In a third combination, the first channel member 10 is made of polystyrene, and the second channel member 20 is made of polyether ether ketone. In a fourth combination, the first channel member 10 is made of polyphenylene sulfide, and the second channel member 20 is made of polyether ether ketone.

The first combination is a preferred combination of materials of the first and second channel members 10 and 20. Using the first combination can improve the workability and biocompatibility of the first and second channel members 10 and 20. Further, the first combination ensures high transparency of the first and second channel members 10 and 20. This allows internal fluid flow to be easily observed without detaching the second channel member 20 from the first channel member 10. By using different materials for the first and second channel members 10 and 20 as described above, the first channel member 10 can be improved in impact resistance and wear resistance, and the second channel member 20 can be made of a soft material to allow for easy mating with the first channel member 10.

<Filter>

The filter 30 is used to separate a target substance included in a fluid from the fluid. As illustrated in FIG. 3, the filter 30 is attached inside the second channel member 20, and positioned at the opening 22 of the discharge channel 23 of the second channel member 20. The filter 30 is disposed along the groove 17. In the exemplary Embodiment 1, the filter 30 is a porous membrane made of metal. The bottom surface of the filter 30 is preferably coplanar with the abutting surfaces 21 and 28.

Figure 7:
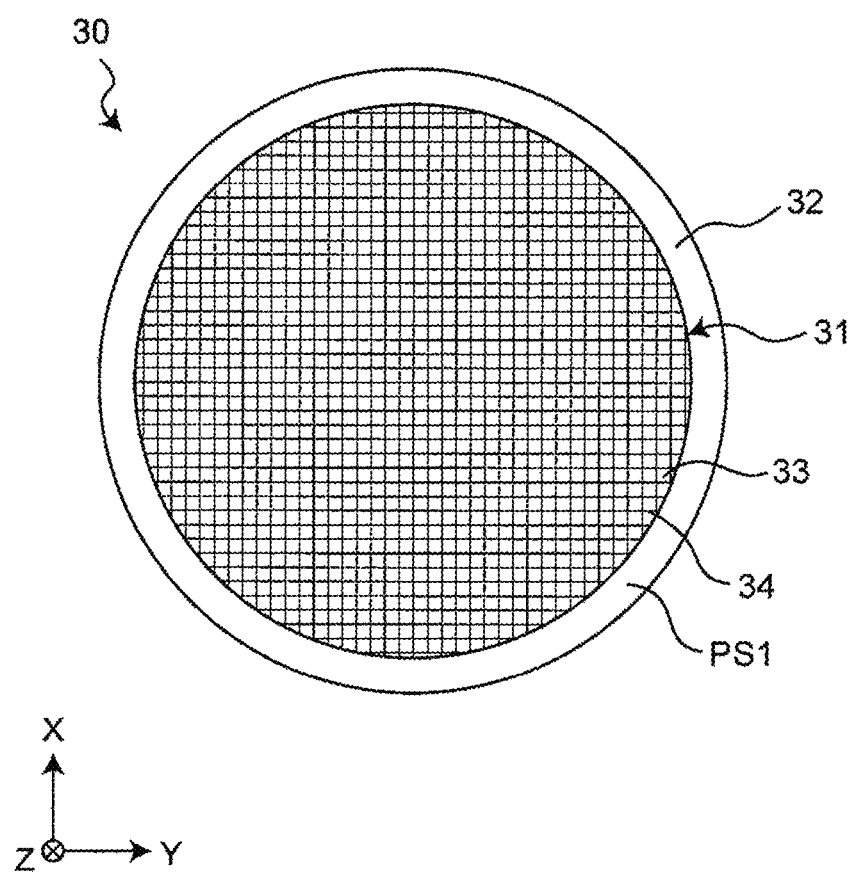
FIG. 7 is a schematic plan view of a filter according to Embodiment 1 of the present invention.
Figure 8:
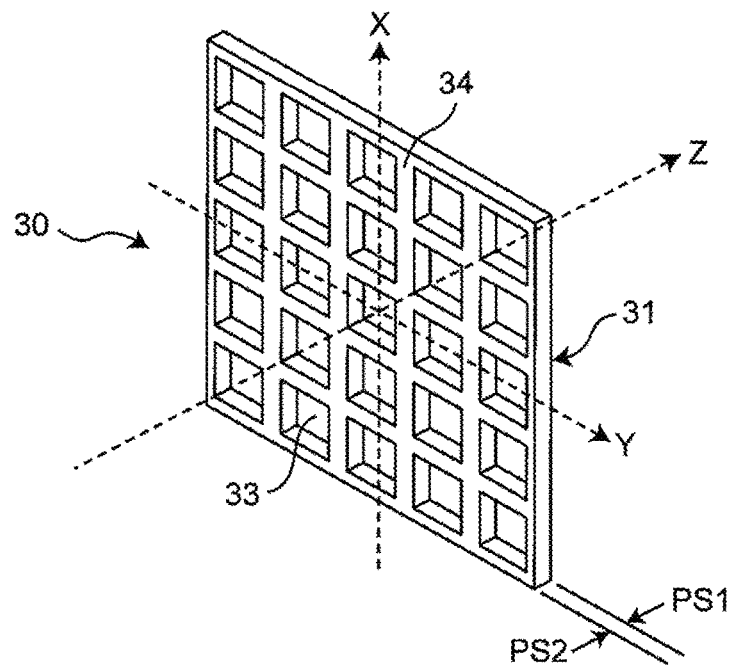
FIG. 8 is an enlarged perspective view of a portion of the filter according to Embodiment 1 of the present invention.

FIG. 7 is a schematic plan view of the filter 30. FIG. 8 is an enlarged perspective view of a portion of the filter 30. The X, Y, and Z directions in FIGS. 7 and 8, which correspond to the X, Y, and Z directions in FIG. 2A, respectively represent the lateral, longitudinal, and thickness directions of the filter 30. As illustrated in FIG. 7, the filter 30 includes a filtering part 31, and a holding part or frame 32 disposed on the outer periphery of the filtering part 31. As illustrated in FIG. 8 (which shows a square section of the filtering part 31), the filter 30 has a first major surface PS1, and a second major surface PS2 that face each other. The first major surface PS1 is located adjacent to the third channel 13, and the second major surface PS2 is located adjacent to the discharge channel 23. In Embodiment 1, the first major surface PS1 of the filter 30, and the projecting surface 21 of the projection 27 of the second channel member 20 are in the same plane (flush with each other). The filtering part 31 includes a filtering body part 34 which includes a plurality of through-holes 33 that extend through the first major surface PS1 and the second major surface PS2.

The filtering body part 34, which forms the body portion of the filter 30, is made of a material mainly containing a metal and/or a metal oxide. For example, the filtering body part 34 may be made of gold, silver, copper, platinum, nickel, palladium, titanium, or an alloy or oxide thereof.

The filter 30 can have, by way of example, a circular, rectangular, or elliptical outer shape. In Embodiment 1, the filter 30 has a substantially circular outer shape. The term "substantially circular" as used herein refers to a shape such that the ratio of the length along the major axis to the length along the minor axis ranges from 1.0 to 1.2.

The filtering part 31 is preferably a plate-like structure provided with the through-holes 33. The filtering part 31 has, by way of example, a circular, rectangular, or elliptical shape. In Embodiment 1, the filtering part 31 has a substantially circular shape.

Figure 9:
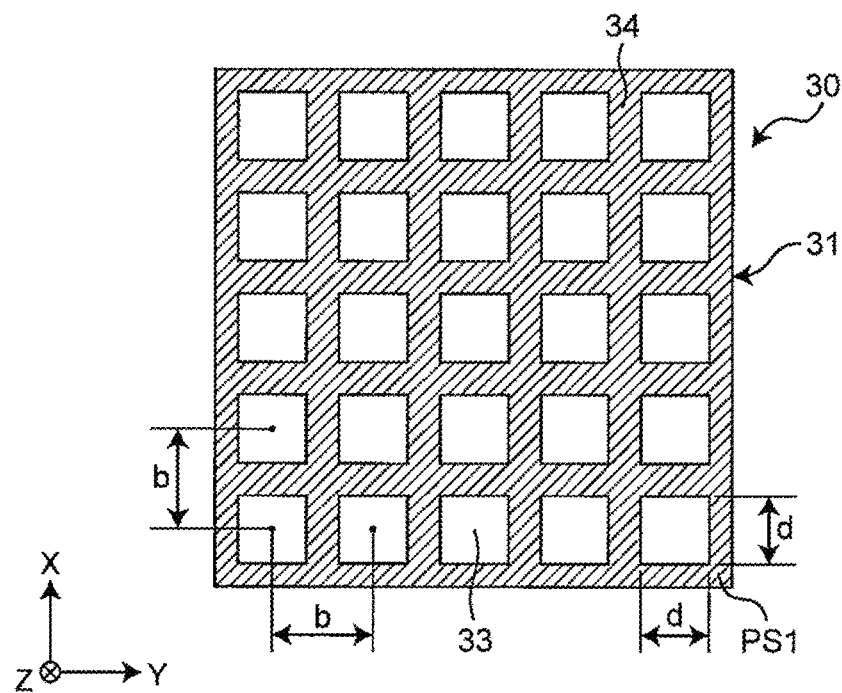
FIG. 9 is a schematic plan view of a portion of the filter illustrated in FIG. 7 as seen in the direction of its thickness.

FIG. 9 is a schematic plan view of a portion of the filtering part 31 as seen in the direction of its thickness (+Z direction). As illustrated in FIG. 9, the through-holes 33 are arranged periodically in the first and second major surfaces PS1 and PS2 of the filtering part 31. More specifically, the through-holes 33 are arranged in the filtering part 31 in a matrix at regular intervals.

In Embodiment 1, the through-holes 33 have a square shape as viewed from the first major surface PS1 of the filtering part 31, that is, as viewed in the +Z direction. The through-holes 33 may not necessarily have a square shape as viewed in the +Z direction, but may have another shape, such as a rectangular, circular, or elliptical shape.

In Embodiment 1, the through-holes 33 have a rectangular shape (in cross section) as projected onto a plane perpendicular to the first major surface PS1 of the filtering part 31. More specifically, the cross-section of the through-holes 33 is a rectangle whose one side in the radial direction of the filter 30 is longer than one side in the thickness direction of the filter 30. Each through-hole 33 may not necessarily have a rectangular cross-section but may have, for example, a tapered cross-section such as a parallelogram or a trapezoid, or may have a cross-section that is symmetrical or asymmetrical with respect to the center of the through-hole 33.

In Embodiment 1, the through-holes 33 are arrayed with equal pitches in two directions parallel to the sides of their square shape as viewed from the first major surface PS1 of the filtering part 31 (+Z direction), that is, in the X and Y directions in FIG. 9. Arranging the through-holes 33 in a square lattice array as described above allows for increased open area percentage, and consequently reduced resistance of the filter 30 to the passage of fluid. This configuration helps shorten filtration time, and reduce stress on the cell.

The through-holes 33 may not necessarily be arranged in a square lattice array, but may be arranged in, for example, a quasi-periodic array or periodical array. Examples of periodic arrays may include any quadrangular arrays, such as rectangular arrays with different pitches in two array directions, and triangular or regular triangular lattice arrays. The through-holes 33 may be arrayed in any fashion as long as the filtering part 31 is provided with a plurality of through-holes 33.

The pitch of the through-holes 33 is designed as appropriate in accordance with the type (e.g., size, morphology, properties, or elasticity) and volume of the cells to be separated. The pitch of the through-holes 33 is herein defined as described below. As illustrated in FIG. 9, with the through-holes 33 viewed from the first major surface PS1 of the filtering part 31, the pitch of the through-holes 33 refers to the distance b between the center of a given through-hole 33 and the center of the adjacent through-hole 33. For periodically arrayed structures, the pitch b of the through-holes 33 is, for example, more than 1 time and not more than 10 times the size of one side "d" of each through-hole 33, preferably not more than 3 times the size of one side "d" of each through-hole 33. Alternatively, the filtering part 31 has an open area percentage of, for example, 10% or more, preferably 25% or more. This configuration can reduce the resistance of the filtering part 31 to the passage of fluid. This helps shorten filtration time, thus reducing stress on the cells. The open area percentage is calculated as the area occupied by the through-holes 33 divided by the projected area of the first major surface PS1 that is assumed to have no through-hole 33.

The filtering part 31 preferably has a thickness more than 0.1 times and not more than 100 times the size (of the one side "d") of each through-hole 33. More preferably, the filtering part 31 has a thickness more than 0.5 times and not more than 10 times the size (of the one side "d") of each through-hole 33. This configuration can reduce the resistance of the filter 30 to the passage of fluid, thus shortening filtration time. As a result, stress on the cell can be reduced.

In the filtering part 31, the first major surface PS1 in contact with the fluid including the target substance preferably has a small surface roughness. The term surface roughness as used herein refers to the mean of the differences between the maximum and minimum values measured with a stylus profilometer at five given points on the first major surface PS1. In Embodiment 1, the surface roughness is preferably less than the size of the cell, more preferably less than half the size of the cell. In other words, the openings defined in the first major surface PS1 of the filtering part 31 by the through-holes 33 are formed in the same plane (XY-plane). The filtering body part 34, which is a portion of the filtering part 31 with no through-hole 33, is formed as a continuous, integral part. This configuration helps reduce deposition of the cell on the surface (first major surface PS1) of the filtering part 31, thus reducing resistance to fluid flow.

In the filtering part 31, the opening of each through-hole 33 in the first major surface PS1 communicates with the opening of the through-hole 33 in the second major surface PS2 via a continuous wall surface. More specifically, each through-hole 33 is provided such that the opening of the through-hole 33 in the first major surface PS1 can be projected onto the opening of the through-hole 33 in the second major surface PS2. In other words, each through-hole 33 is provided such that, with the filtering part 31 viewed from the first major surface PS1, the opening of the through-hole 33 in the first major surface PS1 overlaps the opening of the through-hole 33 in the second major surface PS2. In Embodiment 1, each through-hole 33 is provided such that its inner wall is perpendicular to the first and second major surfaces PS1 and PS2.

The holding part 32 is disposed on the outer periphery of the filtering part 31. The holding part 32 may be thicker than the filtering part 31. This configuration can increase the mechanical strength of the filter 30.

The holding part 32 is preferably ring-shaped as viewed from the first major surface PS1 of the filtering part 31. With the filter 30 viewed from the first major surface PS1, the center of the holding part 32 coincides with the center of the filtering part 31. In other words, the holding part 32 is formed concentrically with the filtering part 31. Information on the filter (e.g., the dimensions of the through-holes 33) may be indicated on the holding part 32.

Figure 10:
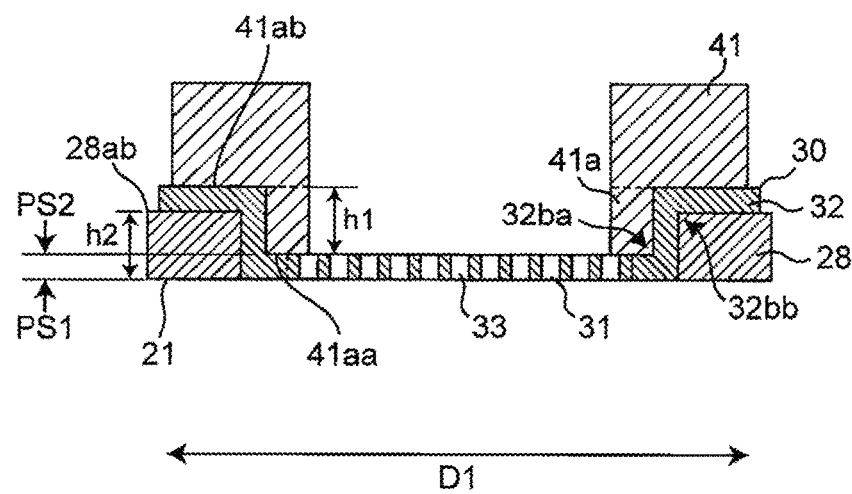
FIG. 10 is an enlarged cross-sectional view of the filter illustrated in FIG. 6.

FIG. 10 is an enlarged cross-sectional view of the filter 30 illustrated in FIG. 6. As illustrated in FIG. 10, the holding part 32 is formed by bending the outer periphery portion of the filter 30 in the direction of the second major surface PS2. The holding part 32 is a portion of the filter 30 positioned closer to the outer edge of the filter 30 than the position where the filtering part 31 begins to bend. In Embodiment 1, the holding part 32 has a first bent part 32*ba*, and a second bent part 32*bb*. The first bent part 32*ba* is a portion of the holding part 32 that is bent in the direction of the second major surface PS2 of the filtering part 31. The second bent part 32*bb* is a portion of the holding part 32 located closer to the outer edge of the filter 30 than the first bent part 32*ba* and bent in a direction of extension Dl in which the filtering part 31 extends. In Embodiment 1, the first bent part 32*ba* is bent in the direction of the second major surface PS2 from the first major surface PS1 of the filtering part 31. The second bent part 32*bb* is bent in a direction parallel to the first and second major surfaces PS1 and PS2 of the filtering part 31. Thus, in the area between the first bent part 32*ba* and the second bent part 32*bb*, the holding part 32 extends in the direction of the second major surface PS2 from the first major surface PS1 of the filtering part 31. In the area closer to the outer edge of the filter 30 than the second bent part 32*bb*, the holding part 32 extends in the direction Dl in which the filtering part 31 extends, that is, in the direction parallel to the first and second major surfaces PS1 and PS2 of the filtering part 31. The direction Dl in which the filtering part 31 of the filter 30 extends includes a direction toward the outer edge of the filter 30, and a direction away from the outer edge of the filter 30. In Embodiment 1, as described above, the second bent part 32*bb* of the holding part 32 is bent toward the outer edge of the filter 30 relative to the first bent part 32ba. The first bent part 32ba and the second bent part 32bb may be, for example, bent in an arcuate shape, or bent at an obtuse angle.

The filter 30 is sandwiched between a first frame part 28 of the second channel member 20, and a second frame part 41 of the holder 40.

<First Frame Part>

The first frame part 28 is formed inside the second channel member 20, and used to sandwich the holding part 32 of the filter 30 between the first frame part 28 and the second frame part 41 of the holder 40. More specifically, the first frame part 28 protrudes from the side wall of the discharge channel 23. The first frame part 28 is formed in an annular (e.g., circular ring) shape, and adapted to receive the second frame part 41 of the holder 40 with the holding part 32 of the filter 30 sandwiched therebetween. The first frame part 28 is located closer to the outer edge of the filter 30 than the boundary between the filtering part 31 and the holding part 32. The first frame part 28 is in contact with a side of the holding part 32 located proximate to the first major surface PS1 of the filter 30. The boundary between the filtering part 31 and the holding part 32 is the position where the filter 30 begins to bend in the direction of the second major surface PS2 in the outer periphery portion of the filter 30. In Embodiment 1, the first frame part 28 is located outward in the direction of extension D1 relative to the bending position of the first bent part 32ba. At a location proximate to the first major surface PS1 of the filter 30, the first frame part 28 is in contact with the holding part 32 but not in contact with the filtering part 31. In Embodiment 1, with the holder 40 viewed in the Z direction, the space enclosed by the first frame part 28 serves as the opening 22 of the discharge channel 23.

<Second Frame Part>

The second frame part 41 is provided on the outer wall surface of the holder 40, and used to sandwich the holding part 32 of the filter 30 between the second frame part 41 and the first frame part 28. More specifically, the second frame part 41 is formed in a cylindrical shape. The second frame part 41 has, in its inner periphery portion, a first stepped part 41a that projects toward a portion of the filtering part 31 of the filter 30. The second frame part 41 is located inside the first frame part 28 with the holding part 32 of the filter 30 sandwiched therebetween. The first stepped part 41a of the second frame part 41 is fit inside the first frame part 28. More specifically, at a location proximate to the second major surface PS2 of the filter 30, the second frame part 41 is in contact with an area extending over a portion of the holding part 32 and a portion of the filtering part 31.

The first stepped part 41a of the second frame part 41 serves to push the filtering part 31 in the direction of the first major surface PS1 from the second major surface PS2, thus regulating the position of the first major surface PS1 of the filtering part 31.

The first stepped part 41a, which projects toward a portion of the filtering part 31, has a first contact surface 41aa that pushes the filtering part 31 in the direction of the first major surface PS1 from the second major surface PS2. Although a side of the filtering part 31 defining the second major surface PS2 contacts the second frame part 41, a side of the filtering part 31 defining the first major surface PS1 does not contact the first frame part 28. This means that the position of the filtering part 31 is not restricted by the first frame part 28. Thus, varying the height h1 of the first stepped part 41a of the second frame part 41 makes it possible to freely determine the position where the filtering part 31 is to be held. In other words, varying the height h1 of the first stepped part 41a of the second frame part 41 makes it possible to freely determine the position of the first major surface PS1 of the filtering part 31. The height h1 of the first stepped part 41a is herein defined as the distance between the first contact surface 41aa of the first stepped part 41a of the second frame part 41, and a second contact surface 41ab of the second frame part 41.

In Embodiment 1, the height of the first stepped part 41a is determined such that the first major surface PS1 of the filtering part 31 is substantially flush with the projecting surface 21. More specifically, the height h1 of the first stepped part 41a is substantially equal to the distance h2 between a third contact surface 28ab of the first frame part 28 and the projecting surface 21. The expression "substantially equal" as used herein means that the difference between the distance h1 and the distance h2 is within the range of ±10%.

[Operation]

Figure 11:
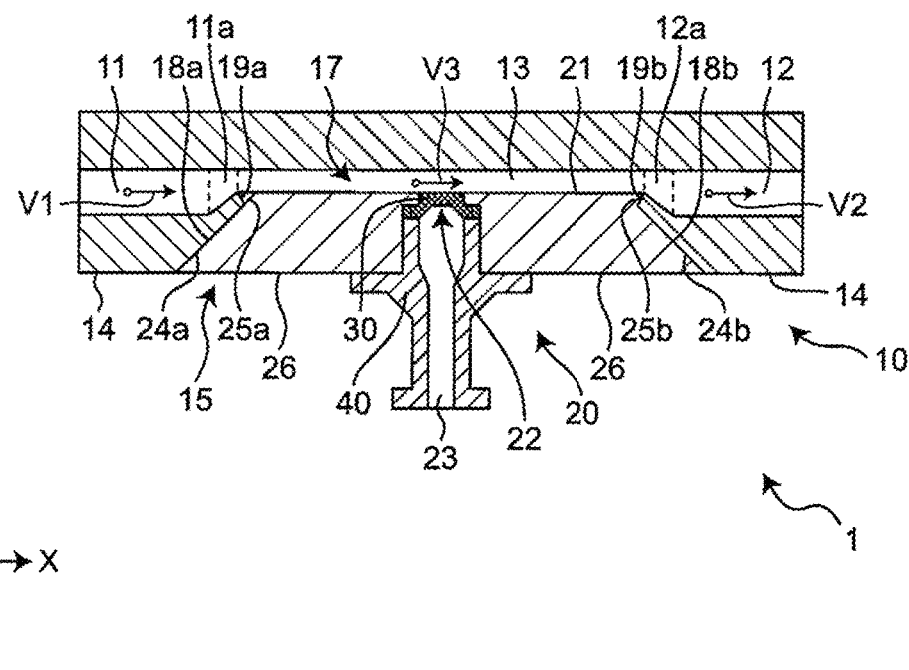
FIG. 11 is a cross-sectional view of the filtration device illustrated in FIG. 3, illustrating fluid flow through the filtration device.

The following describes, with reference to FIG. 11, how the filtration device 1 operates in filtering the fluid including the target substance. FIG. 11 is a cross-sectional view of the filtration device 1 depicted in FIG. 3, illustrating an example of fluid flow in the filtration device 1. As illustrated in FIG. 11, when in use, the filtration device 1 is placed such that the outer wall surface 26 of the second channel member 20 faces down, that is, the discharge channel 23 extends downward (relative to gravity). In the first channel member 10 of the filtration device 1, the fluid including the target substance flows from the first channel 11 to the second channel 12 via the third channel 13. A portion of the fluid flowing in the third channel 13 undergoes cross-flow filtration by the filter 30, and is discharged to the discharge channel 23. At this time, due to the smaller cross-sectional area of the third channel 13 than the first and second channels 11 and 12, the fluid flows through the third channel 13 at a velocity V3 higher than the velocities V1 and V2 at which the fluid respectively flows through the first and second channels 11 and 12.

In the first connection part 11a connecting the first channel 11 with the groove 17, and in the second connection part 12a connecting the second channel 12 with the groove 17, the first and second channels 11 and 12 decrease in cross-sectional area with increasing proximity to the groove 17. This configuration helps prevent an abrupt change in the velocity of fluid flow from the first channel 11 to the third channel 13, and an abrupt change in the velocity of fluid flow from the third channel 13 to the second channel 12.

The mating between the first channel member 10 and the second channel member 20 is achieved by bringing the recessed surface 16 of the recess 15 and the projecting surface 21 of the projection 27 into surface contact with each other. This configuration helps keep the fluid in the third channel 13 from leaking out through the recessed surface 16. The mating between the first channel member 10 and the second channel member 20 is also achieved by bringing the recessed mating surface 18 and the projecting mating surface 24 into surface contact with each other. More specifically, the mating between the first channel member 10 and the second channel member 20 is achieved by bringing the first sloped surface 18a and the third sloped surface 24a into surface contact with each other, and brining the second sloped surface 18b and the fourth sloped surface 24b into surface contact with each other. This configuration helps keep the fluid in the third channel 13 from leaking out through the recessed mating surface 18.

[Effects]

The filtration device 1 according to Embodiment 1 can provide effects described below.

The filtration device 1 includes the first channel member 10, the second channel member 20, and the filter 30. The first channel member 10 has the recess 15, the groove 17, the first and second channels 11 and 12, and the first and second connection parts 11a and 12a. The recess 15 is recessed inward from the first outer wall surface 14. The groove 17 has the opening 17a in the recessed surface 16 of the recess 15. The first and second channels 11 and 12 are each defined by a through-hole connected to the groove 17. The second channel member 20 has the projection 27 that detachably mates with the recess 15 of the first channel member 10. The second channel member 20 includes the discharge channel 23 that has the opening 22 in the projecting surface 21 of the projection 27 placed over the groove 17 of the first channel member 10. The filter 30 is disposed along the groove 17 of the first channel member 10, and positioned at the opening 22 of the discharge channel 23 of the second channel member 20. The third channel 13 is formed by positioning the projecting surface 21 of the projection 27 of the second channel member 20 over the opening 17a of the groove 17 of the first channel member 10. The third channel 13 is connected to the first channel 11 via the first connection part 11a, and connected to the second channel 12 via the second connection part 12a. The third channel 13 at which the filter 30 is positioned has a smaller cross-sectional area than the first channel 11.

The above-mentioned configuration makes it possible to minimize an increase in the velocity of the fluid through the first and second channels 11 and 12 while increasing the velocity of the fluid through the third channel 13 that faces the filter 30. This helps reduce clogging of the filter 30 by the target substance, and also reduce bubbling of the fluid (liquid) to be filtered. If the target substance is a cell, the above-mentioned configuration also helps minimize a decrease in the activity of the cell or damage to the cell.

The filtration device 1 is formed by the first and second channel members 10 and 20 that are separate from each other. This configuration allows the cross-sectional area of the third channel 13 to be changed easily by changing the shape of the second channel member 20. For example, the projecting surface 21 of the projection 27 of the second channel member 20 may be provided with a protruding portion, and the protruding portion may be extended to the vicinity of the lower end portion (end portion in the –Z direction) of the groove 17 to further reduce the cross-sectional area of the third channel 13. The above-mentioned configuration also allows the third channel 13 to be easily formed by the first channel member 10 and the second channel member 20. Further, the second outer wall surface of the first channel member 10, which is the wall surface opposite to the first outer wall surface 14, is placed on a placement surface. This configuration helps ensure that, when the second channel member 20 is detached from the first channel member 10, the target substance can be observed and sampled while allowing the first channel member 10 to keep storing the fluid including the target substance. Further, the fluid including the target substance can be easily collected from the groove 17.

In the filtration device 1, the recess 15 and the projection 27 may be detachably mated with each other without using another intervening component.

The above-mentioned configuration eliminates the need for a screw or other such component. The second channel member 20 can be thus easily attached to or detached from the first channel member 10.

In the filtration device 1, the first channel member 10 has the recessed mating surface 18 on the lateral side of the recess 15 to allow mating between the recess 15 and the projection 27. The second channel member 20 has the projecting mating surface 24 on the lateral side of the projection 27 to allow mating between the recess 15 and the projection 27. The recessed mating surface 18 includes the notches 19a and 19b recessed inwardly of the first channel member 10. The projecting mating surface 24 includes the protrusions 25a and 25b, which protrude outwardly of the second channel member 20 and respectively mate with the notches 19a and 19b. The second channel member 20 is detachably attached to the first channel member 10 by mating the protrusions 25a and 25b respectively with the notches 19a and 19b.

The above-mentioned configuration facilitates detachably attaching the second channel member 20 to the first channel member 10.

In the filtration device 1, the recessed mating surface 18 defines the sloped surfaces 18a and 18b inclined with respect to the recessed surface 16 of the recess 15. The projecting mating surface 24 defines the sloped surfaces 24a and 24b inclined with respect to the projecting surface 21 of the projection 27 that contacts the recessed surface 16 of the recess 15. The mating between the first channel member 10 and the second channel member 20 is achieved by bringing the recessed mating surface 18 and the projecting mating surface 24 into surface contact with each other.

The above-mentioned configuration helps ensure that, at the location of the lateral side of the recess 15, the first channel member 10 and the second channel member 20 make contact over an increased area. This helps further reduce leakage of the fluid flowing in the third channel 13.

In the filtration device 1, the recessed surface 16 of the recess 15 of the first channel member 10 defines a flat surface. The projecting surface 21 of the projection 27 of the second channel member 20 defines a flat surface. The mating between the first channel member 10 and the second channel member 20 is achieved by bringing the recessed surface 16 of the recess 15 and the projecting surface 21 of the projection 27 into surface contact with each other.

The above-mentioned configuration helps ensure that, at the location of the recessed surface 16 of the recess 15, the first channel member 10 and the second channel member 20 make contact over an increased area. This helps further reduce leakage of the fluid flowing in the third channel 13.

In the filtration device 1, the filter 30 has the first major surface PS1 and the second major surface PS2 that face each other. The first major surface PS1 is located adjacent to the third channel 13, and the second major surface PS2 is located adjacent to the discharge channel 23. The first major surface PS1 and the projecting surface 21 are flush with each other.

The above-mentioned configuration helps increase the velocity at which the fluid flows near the filter 30.

In the filtration device 1, the second channel 12 has a larger cross-sectional area than the third channel 13.

The above-mentioned configuration helps minimize an increase in flow velocity through the second channel 12.

In the filtration device 1, the filter 30 is attached to the second channel member 20.

The above-mentioned configuration allows the filter 30 to be easily replaced by detaching the second channel member 20 from the first channel member 10.

In the filtration device 1, the groove 17 is provided linearly.

The above-mentioned configuration helps increase the velocity at which the fluid flows through the third channel 13 defined by the groove 17.

The present invention is not limited to Embodiment 1 but may be practiced in various other forms. Although the foregoing description of Embodiment 1 is directed to the case where the first and second channels 11 and 12 have the same cross-sectional area, this is not to be construed restrictively. The first and second channels 11 and 12 may have different cross-sectional areas.

Figure 12:
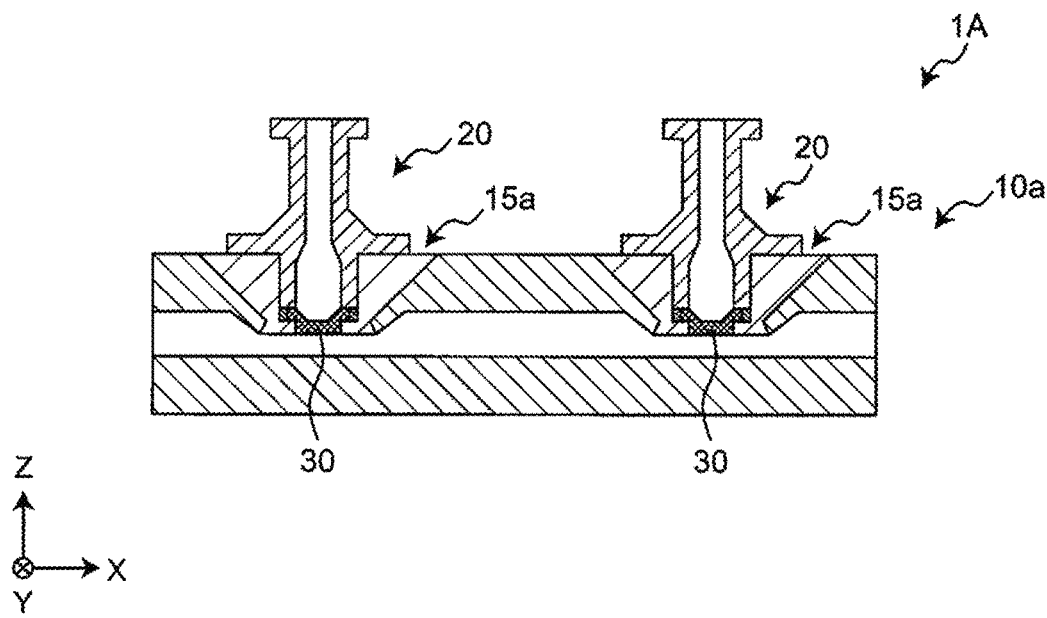
FIG. 12 is a schematic cross-sectional view of a filtration device according to a modification.

Although the foregoing description of Embodiment 1 is directed to the case where the first channel member 10 has a single recess 15, this is not to be construed restrictively. FIG. 12 is a schematic cross-sectional view of a filtration device 1A according to a modification. As illustrated in FIG. 12, a first channel member 10a of the filtration device 1A may have a plurality of recesses 15a. Each recess 15a of the first channel member 10a mates with the second channel member 20 to which the filter 30 is attached. This configuration makes it possible to use a plurality of filters 30 to filter the fluid. This allows the fluid to be filtered with further improved efficiency.

Although the foregoing description of Embodiment 1 is directed to the case where the angle θ1 formed by the first sloped surface 18a and the recessed surface 16, and the angle θ2 formed by the second sloped surface 18b and the recessed surface 16 are 45 degrees, this is not to be construed restrictively. The angles θ1 and θ2 may not necessarily be 45 degrees. The angles θ1 and θ2 may differ from each other.

Although the foregoing description of Embodiment 1 is directed to the case where the first notch 19a is provided in an end portion of the first sloped surface 18a located adjacent to the recessed surface 16, and the second notch 19b is provided in an end portion of the second sloped surface 18b located adjacent to the recessed surface 16, this is not to be construed restrictively. The first notch 19a may be provided in a portion of the first sloped surface 18a other than the end portion located adjacent to the recessed surface 16. The second notch 19b may be provided in a portion of the second sloped surface 18b other than the end portion located adjacent to the recessed surface 16.

Although the foregoing description of Embodiment 1 is directed to the case where the first notch 19a is inclined with respect to the Z-axis by two degrees in the +X direction, and the second notch 19b is inclined with respect to the Z-axis by two degrees in the −X direction, this is not to be construed restrictively. Although the foregoing description is directed to the case where the first protrusion 25a is inclined with respect to the Z-axis by two degrees in the +X direction, and the second protrusion 25b is inclined with respect to the Z-axis by two degrees in the −X direction, this is not to be construed restrictively. The first notch 19a, the second notch 19b, the first protrusion 25a, and the second protrusion 25b may not necessarily be inclined by two degrees.

Figure 13:
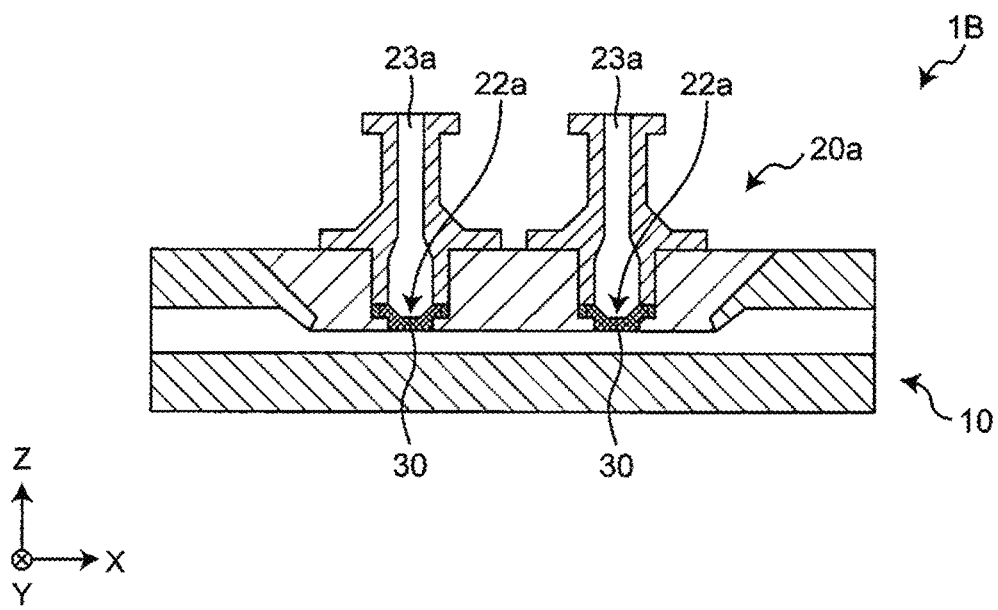
FIG. 13 is a schematic cross-sectional view of a filtration device according to another modification.

Although the foregoing description of Embodiment 1 is directed to the case where the second channel member 20 is provided with a single opening 22, this is not to be construed restrictively. FIG. 13 is a schematic cross-sectional view of a filtration device 1B according to a modification. As illustrated in FIG. 13, a second channel member 20a may be provided with a plurality of discharge channels 23a each having an opening 22a, with the filter 30 attached to the opening 22a of each discharge channel 23a. This configuration makes it possible to use a plurality of filters 30 to filter the fluid. This allows the fluid to be filtered with improved efficiency.

Although the foregoing description of Embodiment 1 is directed to the case where the first outer wall surface 14 of the first channel member 10 is flush with the outer wall surface 26 of the second channel member 20 located opposite to the projecting surface 21, and the second outer wall surface of the first channel member 10 located opposite to the first outer wall surface 14 is parallel to the first outer wall surface 14, this is not to be construed restrictively. For example, the outer wall surface 26 of the second channel member 20 may be positioned higher than the first outer wall surface 14 of the first channel member 10 in the +Z direction. The second outer wall surface of the first channel member 10 may be formed in a shape different from the first outer wall surface 14, for example, a curved shape.

Although the foregoing description of Embodiment 1 is directed to the case where, in the first connection part 11a connecting the first channel 11 with the groove 17, and in the second connection part 12a connecting the second channel 12 with the groove 17, the first and second channels 11 and 12 decrease in cross-sectional area with increasing proximity to the groove 17, this is not to be construed restrictively. Other configurations may be employed as long as the first channel member 10 and the second channel member 20 mate with each other such that the third channel 13 has a smaller cross-sectional area than the first channel 11.

Figure 14:
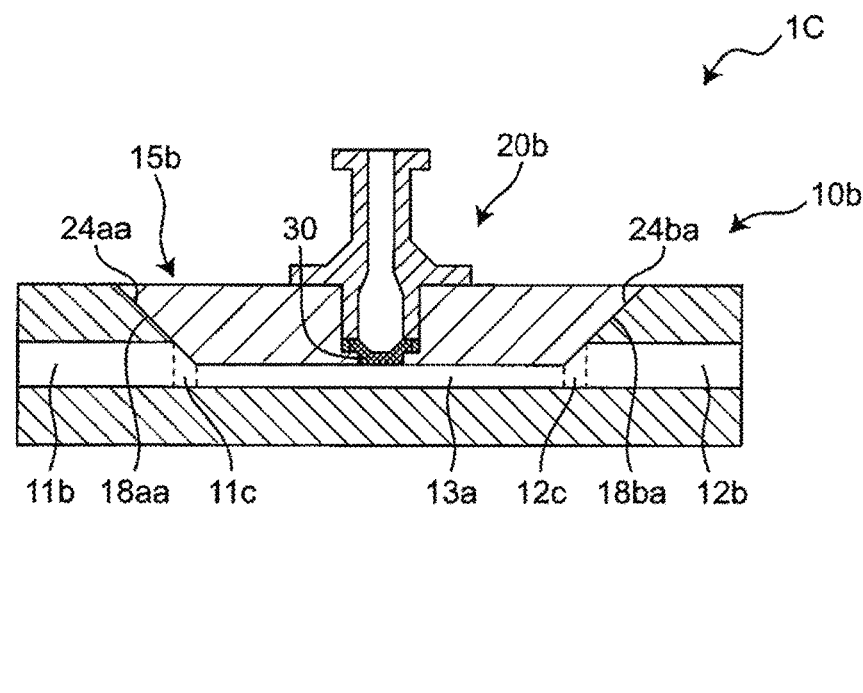
FIG. 14 is a schematic cross-sectional view of a filtration device according to another modification.

FIG. 14 is a schematic cross-sectional view of a filtration device 1C according to a modification. As illustrated in FIG. 14, a third channel 13a may be formed such that, with a recess 15b of a first channel member 10b mated with a second channel member 20b, a portion of a third sloped surface 24aa of the second channel member 20b, and a portion of a fourth sloped surface 24ba of the second channel member 20b respectively reduce the cross-sectional areas of a first channel 11b and a second channel 12b. In other words, a first connection part 11c connecting the first channel 11b with the third channel 13a may be defined by the third sloped surface 24aa of the second channel member 20b. A second connection part 12c connecting the second channel 12b with the third channel 13a may be defined by the fourth sloped surface 24ba of the second channel member 20.

The above-mentioned configuration as well helps reduce clogging of the filter 30 by the target substance, and also reduce bubbling of the fluid (liquid) to be filtered. If the target substance is a cell, the above-mentioned configuration also helps minimize a decrease in the activity of the cell or damage to the cell. The above-mentioned configuration also allows the shape of the third channel 13a to be changed easily by changing the shape of the second channel member 20b. For example, by extending the second channel member 20b toward the lower end portion (end portion in the −Z direction) of the groove 17, the cross-sectional area of the third channel 13a can be further reduced.

Although the foregoing description of Embodiment 1 is directed to the case where the filter 30 is a porous membrane made of metal, this is not to be construed restrictively. The filter 30 may be any filter capable of separating the target substance included in the fluid from the fluid. For example, the filter 30 may be another filter such as a membrane filter.

Although the foregoing description of Embodiment 1 is directed to the case where the fluid including the target substance is a liquid, the invention is not so limited. For example, the fluid may be a gas.

Although the foregoing description of Embodiment 1 is directed to the case where, in the second connection part 12a connecting the second channel 12 with the groove 17, the second channel 12 decreases in cross-sectional area with increasing proximity to the groove 17, the invention is not so limited. For example, the second channel 12, the second connection part 12a, and the third channel 13 may have the same cross-sectional area. This configuration as well makes it possible to minimize an increase in the velocity of the fluid through the first channel 11 while increasing the velocity of the fluid through the third channel 13 that faces the filter 30.

Although the foregoing description of Embodiment 1 is directed to the case where the recessed mating surface 18 includes the notches 19a and 19b, and the projecting mating surface 24 includes the protrusions 25a and 25b, the invention is not so limited. For example, the recessed mating surface 18 may include a protrusion, and the projecting mating surface 24 may include a notch. This configuration as well facilitates the mating between the recess 15 and the projection 27.

Although the foregoing description of Embodiment 1 is directed to the case where the filter 30 is attached to the second channel member 20, the invention is no so limited. As long as the filter 30 is positioned at the third channel 13, the filter 30 may be attached to, for example, the first channel member 10.

Although the foregoing description of Embodiment 1 is directed to the arrangement illustrated in FIG. 1, which represents an example of how filtration is performed by using the filtration device 1, the invention is not so limited. In another arrangement different from the arrangement in FIG. 1, the pump 3 may be disposed within the path of the pipe 53 instead of between the pipe 51 and the pipe 52. Alternatively, a closed container may be used as the fluid tank 2 or the filtrate tank 4 to achieve a closed filtration device.

Although the foregoing description of Embodiment 1 is directed to the case where the second channel member 20 is detachably attached to the first channel member 10 by mating the protrusions 25a and 25b respectively with the notches 19a and 19b, the invention is not so limited. The second channel member 20 may be detachably attached to the first channel member 10 by threaded engagement.

Figure 15:
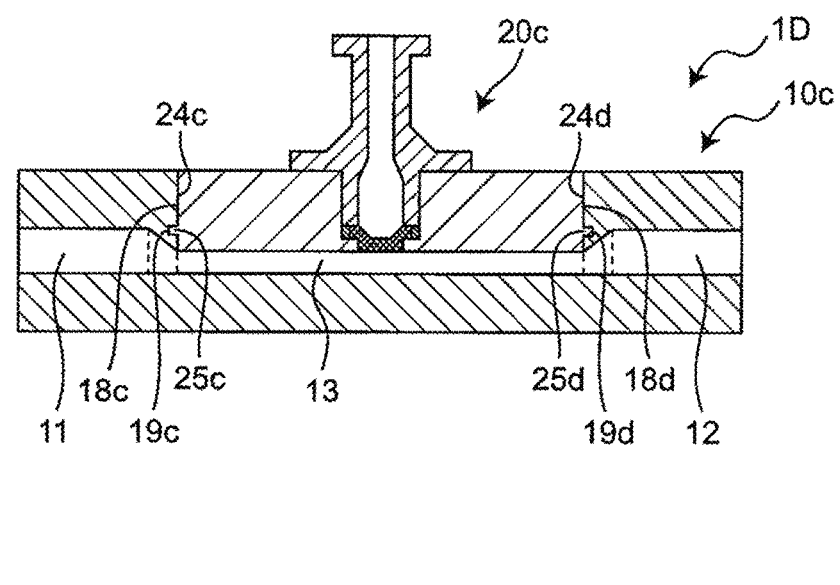
FIG. 15 is a schematic cross-sectional view of a filtration device according to another modification.

Although the foregoing description of Embodiment 1 is directed to the case where the recessed mating surface 18 defines a sloped surface inclined with respect to the recessed surface 16 of the recess 15, and the projecting mating surface 24 defines a sloped surface inclined with respect to the projecting surface 21 of the projection 27 that contacts the recessed surface 16 of the recess 15, the invention is not so limited. For example, the first channel member 10 and the second channel member 20 may be configured as in a filtration device 1D illustrated in FIG. 15. As illustrated in FIG. 15, a recessed mating surface of a first channel member 10c includes a first mating surface 18c, and a second mating surface 18d. The first mating surface 18c and the second mating surface 18d are not formed as inclined surfaces. More specifically, the first mating surface 18c and the second mating surface 18d extend in a direction (Z direction) orthogonal to the direction in which the third channel 13 extends. A projecting mating surface of a second channel member 20c includes a third mating surface 24c, and a fourth mating surface 24d. The third mating surface 24c and the fourth mating surface 24d are not formed as inclined surfaces. More specifically, the third mating surface 24c and the fourth mating surface 24d extend in the direction (Z direction) orthogonal to the direction in which the third channel 13 extends.

The first mating surface 18c includes a first notch 19c notched in a direction (−X direction) in which the first channel 11 extends. The second mating surface 18d includes, in its end portion adjacent to the recessed surface 16, a second notch 19d notched in a direction (+X direction) in which the second channel 12 extends. The third mating surface 24c includes a first protrusion 25c that mates with the first notch 19c of the first channel member 10c, and the fourth mating surface 24d includes a second protrusion 25d that mates with the second notch 19d. This configuration as well facilitates detachably attaching the second channel member 20c to the first channel member 10c.

Although the present invention has been described in sufficient detail by way of a preferred embodiment with reference to the accompanying drawings, various modifications and alterations will be apparent to those skilled in the art. Such modifications and alterations are to be understood as falling within the scope of the invention as defined by the appended claims without departing therefrom.

The filtration device according to the present invention makes it possible to reduce clogging of a filter by a target substance, and also reduce bubbling of the fluid to be filtered. Therefore, the filtration device is useful for applications involving filtration of a fluid including a target substance.

REFERENCE SIGNS LIST 1, 1A, 1B, 1C, 1D filtration device
1a fluid inlet
1b fluid outlet
1c filtrate outlet
2 fluid tank
3 pump
4 filtrate tank
5 target substance
6, 7 fluid
10, 10a, 10b, 10c first channel member
11, 11b first channel
11a, 11c first connection part
11aa first sloped surfaced surface
12, 12b second channel
12a, 12c second connection part
12aa second sloped surfaced surface
13, 13a third channel
14 first outer wall surface
15, 15a, 15b recess
16 recessed surface
17 groove
17a opening
18, 18aa, 18ba recessed mating surface
18a first sloped surface
18b second sloped surface
18c first mating surface
18d second mating surface
19a, 19c first notch
19b, 19d second notch
20, 20a, 20b, 20c second channel member
21 projecting surface
22, 22a opening
23, 23a discharge channel
24 projecting mating surface
24a, 24aa third sloped surface
24b, 24ba fourth sloped surface 24c third mating surface
24d fourth mating surface
25a, 25c first protrusion
25b, 25d second protrusion
26 outer wall surface
27 projection
28 first frame part
28ab third contact surface
30 filter
31 filtering part
32 holding part
32ba first bent part
32bb second bent part
33 through-hole
34 filtering body part
40 holder
41 second frame part
41a first stepped part
41aa first contact surface
41ab second contact surface
51, 52, 53, 54 pipe

The invention claimed is:

1. A filtration device comprising:
   (a) a first channel member including:
      (i) a recess recessed inward from an outer wall surface;
      (ii) a groove formed in a recessed surface of the recess, the groove having an opening;
      (iii) first and second channels defined by respective through-holes connected to the groove;
      (iv) a first connection part connecting the groove with the first channel; and
      (v) a second connection part connecting the groove with the second channel;
   (b) a second channel member removably connected to the first channel member, the second channel member having a projection which includes a projection surface that cooperates with the recess of the first channel member to define a third channel located between the first and second channels of the first channel member, the third channel being connected to the first channel via the first connection part and being connected to the second channel via the second connection part, the third channel having a smaller cross-sectional area than the first channel, the second channel member including a discharge channel located in the projection and having an opening that extends through the projection surface; and
   (c) a filter positioned at the opening of the discharge channel such that the filter is located along the third channel,
   wherein:
   the recessed surface of the recess of the first channel member defines a flat surface;
   the projection surface of the projection of the second channel member defines a flat surface; and
   the first channel member and the second channel member are mated with each other by bringing the recessed surface of the recess and the projecting surface of the projection into surface contact with each other.

2. The filtration device according to claim 1, wherein the recess and the projection are detachably mated with each other without using another intervening component.

3. The filtration device according to claim 2, wherein:
   the first channel member has a recessed mating surface on a lateral side of the recess to allow mating between the recess and the projection;
   the second channel member has a projecting mating surface on a lateral side of the projection to allow mating between the recess and the projection;
   the recessed mating surface includes a notch recessed inwardly of the first channel member;
   the projecting mating surface includes a protrusion, the protrusion protruding outwardly of the second channel member to mate with the notch; and
   the second channel member is detachably attached to the first channel member by mating the protrusion with the notch.

4. The filtration device according to claim 3, wherein:
   the recessed mating surface defines a sloped surface which is inclined with respect to the recessed surface of the recess;
   the projecting mating surface defines a sloped surface which is inclined with respect to the projecting surface of the projection that contacts the recessed surface of the recess; and
   the first and second channel members are mated with each other by bringing the recessed mating surface and the projecting mating surface into surface contact with each other.

5. The filtration device according to claim 1, wherein:
   the filter has a first major surface and a second major surface that face each other;
   the first major surface is disposed adjacent to the third channel;
   the second major surface is disposed adjacent to the discharge channel; and
   the first major surface and the projecting surface are flush with each other.

6. The filtration device according to claim 1, wherein the second channel has a larger cross-sectional area than the third channel.

7. The filtration device according claim 1, wherein the filter is attached to the second channel member.

8. The filtration device according to claim 1, wherein the groove extends linearly.

9. The filtration device according to claim 1, wherein the first channel member includes a plurality of recesses, and each recess mates with the second channel member to which the filter is attached.

10. The filtration device according to claim 1, wherein:
    the discharge channel is a first discharge channel;
    the opening is a first opening;
    the filter is a first filter;
    the second channel member includes a second discharge channel having a second opening that extends through the projection surface;
    a second filter positioned at the second opening of the second discharge channel such that the second filter is located along the third channel.

11. The filtration device according to claim 1, wherein the first, second and third channels are linearly extending.

12. The filtration device according to claim 1, wherein the first and second channels are circular in cross section and the third channel has a semicircular cross section.

* * * * *